US009436990B2

(12) United States Patent
Otani et al.

(10) Patent No.: US 9,436,990 B2
(45) Date of Patent: Sep. 6, 2016

(54) DEFECT OBSERVATION METHOD AND DEVICE THEREFOR

(71) Applicant: Hitachi High-Technologies Corporation, Minato-ku, Tokyo (JP)

(72) Inventors: Yuko Otani, Tokyo (JP); Toshifumi Honda, Tokyo (JP); Shunichi Matsumoto, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 72 days.

(21) Appl. No.: 14/367,186

(22) PCT Filed: Oct. 22, 2012

(86) PCT No.: PCT/JP2012/077244
§ 371 (c)(1),
(2) Date: Jun. 19, 2014

(87) PCT Pub. No.: WO2013/118351
PCT Pub. Date: Aug. 15, 2013

(65) Prior Publication Data
US 2015/0003722 A1 Jan. 1, 2015

(30) Foreign Application Priority Data
Feb. 6, 2012 (JP) .................................. 2012-022941

(51) Int. Cl.
*G06K 9/62* (2006.01)
*G06T 7/00* (2006.01)
(Continued)

(52) U.S. Cl.
CPC ......... *G06T 7/0012* (2013.01); *G01N 21/9501* (2013.01); *G01N 21/956* (2013.01); *G02B 21/0004* (2013.01); *G06T 2207/30141* (2013.01)

(58) Field of Classification Search
None
See application file for complete search history.

(56) References Cited

U.S. PATENT DOCUMENTS 4,342,515 A * 8/1982 Akiba .................. G01B 11/303
356/237.3
6,407,373 B1 6/2002 Dotan
(Continued)

FOREIGN PATENT DOCUMENTS

JP 2000-352697 A 12/2000
JP 2007-225563 A 9/2007
(Continued)

OTHER PUBLICATIONS

English translation of an Office Action mailed Mar. 24, 2015 for related Japanese Patent Application No. 2012-022941.

*Primary Examiner* — Brian P Werner
(74) *Attorney, Agent, or Firm* — Miles & Stockbridge P.C.

(57) ABSTRACT

The present invention is detection of a defect signal which is small enough to be buried in a background noise, by a method that includes detecting a defect on a specimen which is detected by another inspection device by using a detection device equipped with an optical microscope, amending positional information of the defect, observing the defect by using an SEM, wherein the detecting the defect is carried out such that forming stationary waves on the specimen by irradiating the specimen with two illumination lights having the same wavelength from the opposite directions on the same incidence plane at the same incidence angle and cause the two illuminating light to interfere; removing scattered components generated by minute irregularities on the specimen surface by a spatial filter, detecting an image formed by the scattered light not removed by the spatial filter; and processing the detected image to detect the defect.

18 Claims, 7 Drawing Sheets

(51) Int. Cl.
*G01N 21/956* (2006.01)
*G01N 21/95* (2006.01)
*G02B 21/00* (2006.01)

(56) References Cited

U.S. PATENT DOCUMENTS

2008/0151235 A1   6/2008   Oshima et al.
2011/0194101 A1*  8/2011   Tachizaki ........... G01N 21/9501
                                                              356/72
2012/0274931 A1   11/2012  Otani et al.

FOREIGN PATENT DOCUMENTS

| JP | 2008-157638 A | 7/2008 |
| JP | 2010-96554 A | 4/2010 |
| JP | 2011-106974 A | 6/2011 |
| WO | WO 2010/044351 A1 | 4/2010 |

* cited by examiner

DEFECT OBSERVATION METHOD AND DEVICE THEREFOR

BACKGROUND

The present invention relates to a defect observation method and a device therefor in which defects or the like existing on or near a surface of a specimen detected by another defect inspection device are observed.

For example, existence of foreign substances on a semiconductor substrate (wafer) and pattern defects such as short circuits or disconnections (hereinafter, these are collectively described as defects) causes failure such as insulation failure or short circuits of wirings in a manufacturing process of a semiconductor device. With the advanced microfabrication of circuit patterns formed on a wafer, fine defects cause insulation failure of a capacitor and destruction of a gate oxide film or the like. These defects are mixed in various states due to various causes such as those generated from a movable part of a carrier device, generated from a human body, generated by reaction with process gas in a processing device, or mixed in chemicals or materials. Therefore, it is important in the mass production of semiconductor devices that defects generated during the manufacturing process are detected to quickly find out the cause of generation of the defects, and the generation of the defects is stopped.

As a conventional method of seeking the cause of generation of defects, there is a method in which the position of defects is first located by a defect inspection device, and the defects are observed and classified in detail by a review device using an SEM (Scanning Electron Microscope) to be compared with a database in which inspection results obtained in each manufacturing process are stored, so that the cause of generation of the defects is estimated.

In this case, the defect inspection device is an optical defect inspection device that illuminates light on the surface of a semiconductor substrate with a laser and carries out a dark-field observation of scattered light from defects to locate the position of the defects, or an optical appearance inspection device or an SEM inspection device that irradiates light of a lamp or laser or electron beams and detects a bright-field optical image of a semiconductor substrate to be compared with reference information, so that the position of the defects on the semiconductor substrate is located. Such observation methods are disclosed in Japanese Patent Application Laid-Open No. 2000-352697 or Japanese Patent Application Laid-Open No. 2008-157638.

As to a device that observes defects in detail using an SEM, U.S. Pat. No. 6,407,373 describes such a method and a device that using positional information of defects on a specimen detected by another inspection device, the position on the specimen is detected by an optical microscope mounted in the SEM defect observation device and the positional information of defects obtained by detecting with the another inspection device is amended, so that the defects are observed (reviewed) in detail by the SEM defect observation device.

Further, Japanese Patent Application Laid-Open No. 2007-225563 describes optical high-resolution detection using a super-resolution technique by illumination of stationary waves.

Further, Japanese Patent Application Laid-Open No. 2011-106974 describes that the sensitivity of a dark-field optical microscope is increased by arranging a filter having spatial distribution on or near a pupil plane of a detection optical system.

A general optical microscope has a resolution limit caused by a diffraction limit proportional to the wavelength of light due to the wave nature of light. For example, in the case where light having a wavelength of 532 nm is collected by an aplanatic lens with an NA of 0.5, the resolution limit becomes 649 nm. A super-resolution technique is a method of obtaining a high degree of spatial resolution exceeding the resolution limit that is dependent on the wavelength.

As a super-resolution technique, there is a near-field microscopy in which scattered light from evanescent waves that locally exist only near the surface of a specimen are detected when light is irradiated, and a stimulated emission suppression microscopy in which a laser having a wavelength different from that of an excitation laser to emit light of fluorescent molecules and that of a doughnut-shaped excitation laser surrounding the excitation laser is irradiated. However, the near-field optical microscopy is technically difficult, and further the throughput is slow. The stimulated emission suppression microscopy is a microscopy used to capture the light emission of fluorescent. Thus, in the case where a high degree of throughput is required, the stimulated emission suppression microscopy is not used in the present situation when the fluorescent molecules are not observed.

Further, an SIM (Structured illumination Microscopy) using structured illumination with the intensity spatially modulated has recently drawn attention, and fluorescent microscopes using the SIM are sold by Carl Zeiss Inc. and Nikon Corporation. Further, a dark-field SIM is disclosed in Japanese Patent Application Laid-Open No. 2007-225563. The SIM is relatively high in throughput as compared to a near-field optical microscope because a wider area can be irradiated.

With the advanced microfabrication of circuit patterns in response to the needs of high integration in recent manufacturing of LSIs, the sizes of target defects become smaller. In response to this, the dimensions of defects to be detected by an optical defect inspection device are required to be smaller. Under the circumstances, the wavelength of illumination is shortened, the resolution is increased, and the NA (Numerical Aperture) of a detection lens is increased in the optical defect inspection device. There are limitations to the shortening of the wavelength of illumination in the device. As a method of increasing the NA of the detection lens, there is a metamaterial having a negative liquid immersion and a negative refractive index. However, it is difficult to use the liquid immersion in a semiconductor inspection, and it is technically difficult to put the metamaterial to practical use. In the super-resolution technique using the structured illumination, the phase of illumination is modulated, plural signals having different intensity phases are obtained, and the resolution can be improved on the basis of changes of the obtained signals. However, as a detection target becomes smaller in size, it becomes difficult to increase the resolution by the super resolution. Because in the case where signals from the detection target are buried in background noise, changes of the signals from the detection target cannot be captured.

In Japanese Patent Application Laid-Open No. 2000-352697, Japanese Patent Application Laid-Open No. 2008-157638, U.S. Pat. No. 6,407,373, and Japanese Patent Application Laid-Open No. 2011-106974, an observation of defects by an optical microscope using a super-resolution technique is not described. On the other hand, Japanese Patent Application Laid-Open No. 2007-225563 describes a super-resolution technique in which two light fluxes are allowed to interfere with each other on a plane of a specimen to illuminate stationary waves and scattered light is detected so that changes of nanometer-order scattered light is detected. However, Japanese Patent Application Laid-Open No. 2007-225563 does not describe that as in the case of detecting minute defects on a semiconductor substrate, scattered light from minute defects are detected while being separated from background noise generated by nanometer-order minute irregularities on a surface of a specimen.

Accordingly, in order to solve the problems of the conventional technique, the present invention provides a defect observation method and a device therefor in which minute defect signals that are likely to be buried in background noise can be detected while being separated from the background noise, so that much smaller defects on a specimen can be observed.

SUMMARY

According to the present invention, in order to solve the above-described problems of the conventional technique, a space distribution optical element (Japanese Patent Application Laid-Open No. 2011-106974) that irradiates structured illumination on a specimen and that has spatial distribution on or near a pupil plane of a detection optical system is arranged, and scattered light as background noise among those from the specimen on which the structured illumination is irradiated are blocked, so that highly-sensitive super-resolution microscopy can be realized, and defects or the like existing on or near the surface of the specimen detected by a defect inspection device can be observed.

Specifically, according to the present invention, a light is illuminated on a specimen using stationary waves, and the stationary waves are modulated, so that the light is illuminated on the specimen in plural illumination conditions. Then, a light scattered by the illumination or excited fluorescence is detected by a detector through a detection optical system having a space distribution optical element on a pupil plane. Further, the obtained signals are combined in a frequency space, and the combined signal is inversely converted, so that a high-resolution signal can be obtained. Accordingly, highly-sensitive detection of target defects can be realized.

Specifically, in order to solve the above-described problems, the present invention provides a defect observation method including detecting defects on a specimen detected by another inspection device by a detection device having an optical microscope on the basis of positional information of the defects, amending the positional information of the defects on the specimen detected by the another inspection device on the basis of positional information of the defects detected by the detection device having the optical microscope, and observing the defects detected by the another inspection device by using an SEM (Scanning Electron Microscope) on the basis of the amended positional information, wherein the defects on the specimen detected by the another inspection device are detected by the detection device having the optical microscope in such a manner that: forming stationary waves on the specimen by allowing two illumination lights having the same wavelength to enter the same incidence plane of the specimen at the same incidence angle from directions that are opposite to each other interfering with each other; removing scattered light components generated from minute irregularities on the surface of the specimen among scattered light from the specimen on which the stationary waves are formed by a spatial filter; detecting an image of scattered light from the specimen that are not removed by the spatial filter; and processing the detected image of the scattered light to detect the defects on the specimen detected by the another inspection device.

Further, in order to solve the above-described problems, the present invention provides a defect observation method including the steps of: detecting defects on a specimen detected by another inspection device using a detection device having an optical microscope on the basis of positional information of the defects; amending the positional information of the defects on the specimen detected by the another inspection device on the basis of positional information of the defects detected by the detection device having the optical microscope; and observing the defects detected by the another inspection device using an SEM (Scanning Electron Microscope) on the basis of the amended positional information, wherein in the step of detecting the defects on the specimen detected by the another inspection device using the detection device having the optical microscope, including the sub-steps of: forming stationary waves on the specimen by entering two illumination lights having the same wavelength in the same incidence plane of the specimen at the same incidence angle from directions that are opposite to each other and interfering with each other; removing scattered light components generated from minute irregularities on the surface of the specimen among scattered light from the specimen on which the stationary waves are formed by a spatial filter; detecting an image of scattered light from the specimen that are not removed by the spatial filter; repeating the steps from the forming to the detecting plural times by changing the phase of the stationary waves formed on the specimen; producing a combined image from plural images, that are detected by repeating plural times, of the scattered light from the specimen on which the stationary waves with the phase changed are illuminated; and detecting defects on the specimen detected by the another inspection device by processing the produced combined image.

In addition, in order to solve the above-described problems, the present invention provides a defect observation device including: detection unit that has an optical microscope; processing unit that amends positional information of defects on a specimen detected by another inspection device on the basis of a result of detecting the defects on the specimen detected by the another inspection device using the detection means on the basis of the positional information of the defects; defect observation unit that observes the defects on the specimen detected by the another inspection device using an SEM (Scanning Electron Microscope) on the basis of the positional information of the defects on the specimen amended by the processing unit; table unit on which the specimen is mounted and which is movable between the detection unit and the defect observation unit; and control unit that controls the detection unit, the processing unit, the observation unit, and the table unit, wherein the detection unit includes: an illumination subunit that functions in such a manner that two illumination lights having the same wavelength are allowed to enter the same incidence plane of the specimen mounted on the table unit at the same incidence angle from directions that are opposite to each other and are allowed to interfere with each other so that stationary waves are formed on the specimen to illuminate the surface of the specimen; a detection optical system subunit that has a spatial filter that removes scattered light components generated from minute irregularities on the surface of the specimen among scattered light from the surface of the specimen on which the stationary waves formed by the illumination subunit are illuminated and that forms an image of scattered light from the surface of the specimen that are not removed by the spatial filter; and an image detection subunit that detects the image of the scattered light from the surface of the specimen formed by the detection optical system subunit, wherein the control unit detects the defects on the specimen detected by the another inspection device by processing the image of the scattered light from the surface of the specimen detected by the image detection subunit and amends the positional information of the defects on the specimen detected by the another inspection device on the basis of the positional information of the detected defects on the table unit.

According to the present invention, in the case where defects detected by another defect inspection device are observed in detail by a review device using an SEM, minute defects to be observed can be reliably moved to the observation visual field of the SEM, and the throughput of the detailed observation of the defects using the SEM can be improved.

DESCRIPTION OF THE PREFERRED EMBODIMENTS

Hereinafter, an embodiment of the present invention will be described in detail by appropriately using the drawings.

In general, in the case where defects generated on a substrate are observed in a semiconductor device manufacturing process, the observation is performed in accordance with the following defect observation procedure. First, the entire surface of a specimen (semiconductor wafer) is scanned by an inspection device to detect defects existing on the specimen, and the coordinates where the defects exist are obtained. Next, some or all of the defects detected by the inspection device are observed in detail by a review device using an SEM on the basis of the defect coordinates obtained by the inspection device, so that the defects are classified and the cause of the defect is analyzed.

Figure 1:
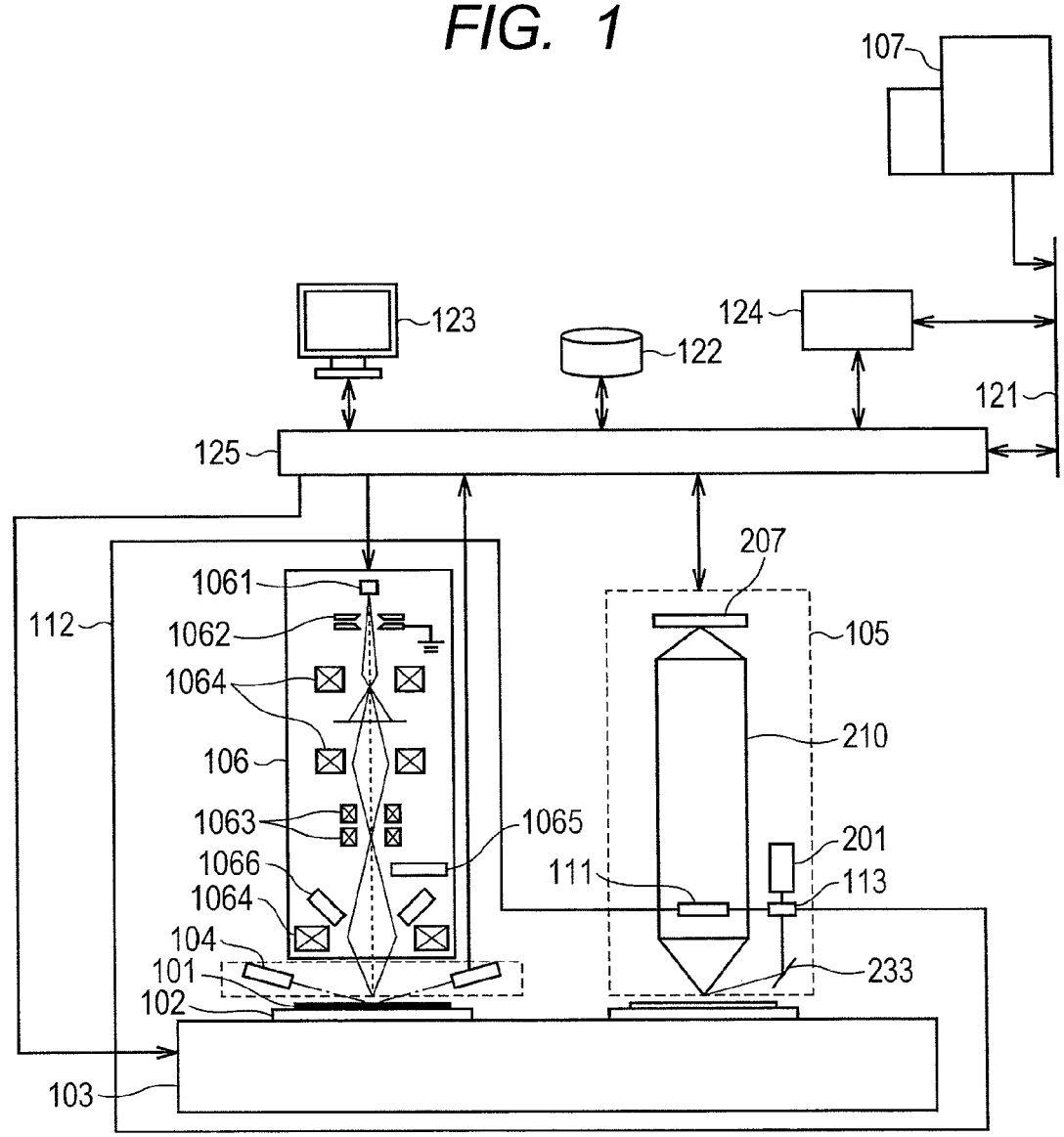
FIG. 1 is a block diagram for showing an outline configuration of a review device in an embodiment of the present invention.

FIG. 1 shows an example of a configuration of a review device 100 using an SEM in the embodiment.

The review device of the embodiment is configured by including a specimen holder 102 on which a specimen (semiconductor wafer) 101 to be inspected is mounted, a stage 103 that allows the specimen holder 102 to be moved so that the entire surface of the specimen 101 can be moved in a viewing field of an SEM 106, the SEM 106 that observes the specimen 101 in detail, an optical height detection system 104 that detects the height of the surface of the specimen 101 to adjust the focal point of the SEM 106 to the surface of the specimen 101, an optical microscope 105 that optically detects defects of the specimen 101 to obtain detailed positional information of the defects on the specimen 101, a vacuum chamber 112 that accommodates the SEM 106 and an objective lens of the optical microscope 105, a control system 125 that controls the SEM 106, the optical height detection system 104, and the optical microscope 105, a user interface 123, a library 122, a network 121 that establishes a connection to a high-order system such as an inspection device 107, and a storage device 124 that stores external data and the like of the inspection device 107 to be supplied to the control system.

The SEM 106 is configured by including therein an electron beam source 1061, an extraction electrode 1062 that extracts and accelerates primary electrons emitted from the electron beam source 1061 in a beam shape, a deflection electrode 1063 that controls the orbits of the primary electron beams extracted and accelerated by the extraction electrode, an objective lens electrode 1064 that converges the primary electron beams with the orbits controlled by the deflection electrode 1063 onto the surface of the specimen 101, a secondary electron detector 1065 that detects secondary electrons generated from the specimen 101 onto which the converged primary electron beams with the orbits controlled are irradiated, and a reflected electron detector 1066 that detects relatively high-energy electrons such as reflected electrons generated from the specimen 101 onto which the converged primary electron beams are irradiated.

The optical microscope 105 is configured by including an illumination optical system 201 that obliquely irradiates light onto the specimen 101, a light collecting optical system 210 that collects light scattered above the specimen 101 among scattered light generated from the surface of the specimen 101 onto which the light is irradiated from the illumination optical system 201, and a detector 207 that detects the scattered light from the specimen 101 collected by the light collecting optical system.

The control system 125 includes an SEM control unit 1251 that controls the SEM 106, an optical microscope control unit 1252 that controls the optical microscope 105, and an entire control unit 1256 that controls the entire review device 100.

Further, the stage 103, the optical height detection system 104, the optical microscope 105, the SEM 106, the user interface 123, the library 122, and the storage device 124 are connected to the control system 125 that is connected to a high-order system (for example, the inspection device 107) via the network 121.

In the review device 100 configured as described above, in particular, the optical microscope 105 has a function of re-detecting (hereinafter, described as detecting) the defects on the specimen 101 detected by the inspection device 107 using the positional information of the defects detected by the inspection device 107, the optical height detection system 104 has a function as focusing means that focuses the primary electron beams to converge the primary electron beams of the SEM 106 onto the surface of the specimen 101, the control system 125 has a function as position correction means that corrects the positional information of the defects detected by inspecting with another inspection device on the basis of the positional information of the defects detected by the optical microscope 105, and the SEM 106 has a function of observing the defects using the positional information corrected by the control system 125. The stage 103 is moved between the optical microscope 105 and the SEM 106 while mounting the specimen 101 thereon, so that the defects detected by the optical microscope 105 can be observed by the SEM 106.

Next, a detailed configuration example of the optical microscope 105 in the embodiment will be described using FIG. 2.

The optical microscope 105 includes an illumination unit 201 having plural illumination optical systems 201a to d, an objective lens 202 that collects the scattered light generated from the specimen 101 illuminated by the plural illumination optical systems 201a to d of the illumination unit 201, a height control mechanism 209 of the objective lens 202, a bright-field illumination optical system 211 having a half mirror 214 that introduces illumination light, a condenser lens 213 for illumination light, and a bright-field light source 212, an imaging optical system 210 that forms an image of the scattered light collected by the objective lens 202 on an imaging element 207, an imaging element 207 that images an image of the scattered light from the specimen 101 formed by the imaging optical system 210, a signal processing unit 221 that processes a signal obtained by the imaging element 207, an image display unit 222 that displays a result obtained by processing with the signal processing unit 221, and a signal storage unit 223 that stores the result obtained by processing with the signal processing unit 221. In addition, the imaging optical system 210 is configured by appropriately including space distribution optical elements 205 and a space distribution optical element switching mechanism 208, to be described later, that selects the space distribution optical element 205 that is most suitable for detection of target defects among those having different optical characteristics.

As the bright-field light source 212, a lamp or a laser can be used. In the case where a laser is used, it is not necessary to use the condenser lens 213. The illumination can be brightened and more scattered light can be introduced to the imaging element 207 by replacing the half mirror 214 with a dichroic mirror.

The ratio of reflection to transmission of the half mirror 214 may be arbitrarily set. However, in the case where the light intensity of the bright-field light source 212 can be sufficiently secured, the half mirror 214 is desirably configured to introduce more scattered light from the defects to the imaging optical system 210 and the imaging element 207. In the case where the bright-field illumination unit is not used, the half mirror 214 may be configured to be movable so as to be removed from an optical axis 301. In this case, more scattered light can be advantageously introduced to the imaging element 207.

The illumination optical system unit 201 includes two sets of illumination optical systems, namely, four illumination optical systems in total, such as a combination of illumination optical systems 201a and 201b and a combination of illumination optical systems 201c and 201d that are disposed so that the illumination lights face each other across the optical axis 301 of the imaging optical system 210. FIG. 2 shows a configuration in which two sets of the combination of illumination optical systems 201a and 201b and the combination of illumination optical systems 201c and 201d are arranged so that the incidence planes of the illumination lights are orthogonal to each other. The incidence plane of the illumination light is a plane orthogonal to the surface of the specimen 101 and parallel to the optical axis of the illumination light entering the specimen 101, and is a plane including therein the optical axis of the illumination light. In many cases, a pattern having a main direction in any one of two directions that are orthogonal to each other is generally formed on the specimen 101. Thus, the illumination light emitted from the respective illumination optical systems are irradiated along the two incidence planes that are orthogonal to each other so as to be associated with the two directions that are orthogonal to each other.

The objective lens 202 and the height control mechanism 209 are installed in the vacuum chamber 112, and the light collected by the objective lens 202 is introduced to the imaging optical system 210 through a vacuum sealed window 111 provided in the vacuum chamber 112.

Although a detailed configuration of the height control mechanism 209 is not illustrated, for example, a configuration in which the height control mechanism 209 is moved using a piezoelectric element, a configuration in which the height control mechanism 209 is moved in the Z-direction (the direction along the optical axis 301 of the imaging optical system 210) along a linear guide using a stepping motor and a ball screw, or a configuration in which the height control mechanism 209 is moved in the Z-direction along a linear guide using an ultrasonic motor and a ball screw can be used.

The arrangement position of the imaging element 207 may be a position conjugate to the surface of the specimen 101 or a position conjugate to a pupil plane of the objective lens 202.

The imaging optical system 210 is configured by appropriately using lenses 203 and 204 that extract an optical image of a pupil plane 302 of the objective lens 202, an imaging lens 206 that forms the optical image of the pupil plane 302 extracted by the lenses 203 and 204 on the imaging element 207, and a space distribution optical element 205 that is inserted into a position conjugate to a pupil plane 303 of the objective lens 202 whose optical image is extracted by the lenses 203 and 204.

The embodiment employs a configuration in which a space distribution optical element holder 208 that holds plural space distribution optical elements 205 having different characteristics and that can switch the space distribution optical elements 205 is inserted into the pupil plane 303. Further, it is not always necessary to arrange the space distribution optical elements 205 on the optical axis 301 of the imaging optical system 210.

Further, the height control mechanism 209 and the imaging element 207 are connected to the control system 125 (FIG. 1) and the signal processing unit 221, respectively.

The lenses 203 and 204 are used to extract the optical image of the pupil plane 302 of the objective lens 202 to the outside to form the optical image of the pupil plane 302 at the conjugate position in the imaging optical system 210.

Further, the space distribution optical element holder 208 can be driven, and the space distribution optical element 205 selected among those held by the space distribution optical element holder 208 is inserted into an optical image same as that on the pupil plane 303 extracted at a position conjugate to the pupil plane 303 in the imaging optical system 210.

Further, in the case where bright-field observation is performed or the space distribution optical elements 205 are not used, the observation is performed while evacuating the space distribution optical elements 205 to a position deviated from the optical path of the imaging optical system in order to avoid disturbance of the obtained image. Alternatively, the space distribution optical element holder 208 may be switched to a position where a parallel flat glass plate having the same thickness as that of each space distribution optical element 205 is installed. The parallel flat glass plate having the same thickness as that of the space distribution optical element 205 is installed to avoid an event that if the space distribution optical elements 205 are removed, the length of the optical path is changed and the image of the specimen 101 is not formed on the imaging element 207. Alternatively, a mechanism that adjusts the position of the imaging lens 206 forming an image or the imaging element 207 and that forms an image on the imaging element 207 may be used without using the parallel flat glass plate.

In the embodiment, the image of the specimen 101 is formed on a detection plane of the imaging element 207 by the combination of the objective lens 202, the lenses 203 and 204, and the imaging lens 206. In the embodiment, the lenses 203 and 204 are used in the imaging optical system 210, but any one of the lenses 203 and 204 may be used and can be appropriately selected.

Next, a configuration example of the illumination optical system unit 201 will be described using FIG. 3A to FIG. 3D.

Figure 2:
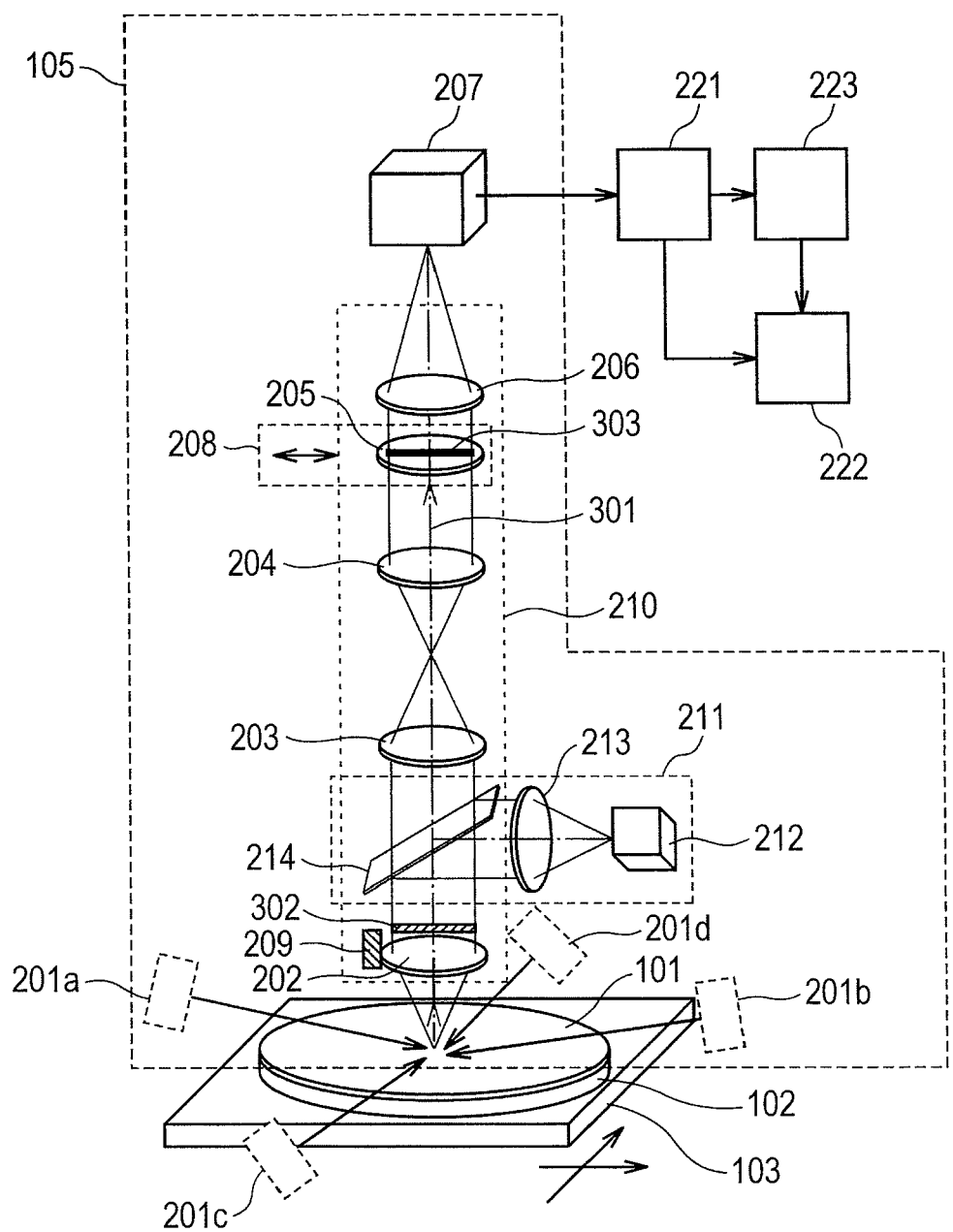
FIG. 2 is a front block diagram for showing an outline configuration of an optical microscope of the review device in the embodiment of the present invention.

In the configuration example shown in FIG. 2, the illumination optical system unit 201 is arranged in such a manner that the illumination optical system unit 201 uses two pairs of illumination optical systems 201a to 201d, the light irradiated from the respective illumination optical systems have the same incidence planes, and are irradiated on the specimen 101 from the directions that are opposite to each other. The light emitted from one pair of illumination optical systems 201a and 201b or 201c and 201d that is arranged to face each other are allowed to interfere with each other on the specimen 101 to produce stationary waves. One pair of illumination optical systems 201a and 201b or 201c and 201d that is arranged to face each other is referred to as an illumination optical system unit set 2011. In the case of the embodiment, two illumination optical system unit sets 2011 are provided. In the case of arranging plural illumination optical system unit sets 2011, the illumination optical system unit sets 2011 are arranged so that the incidence planes of the respective illumination optical system unit sets 2011 are not parallel to each other.

Figure 3A:
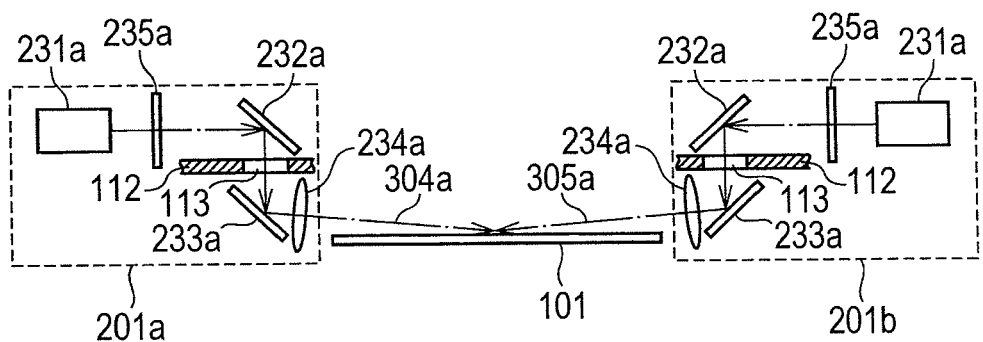
FIG. 3A is a front block diagram for showing an outline configuration of an illumination optical system subunit in the optical microscope of the review device in the embodiment of the present invention.
Figure 3B:
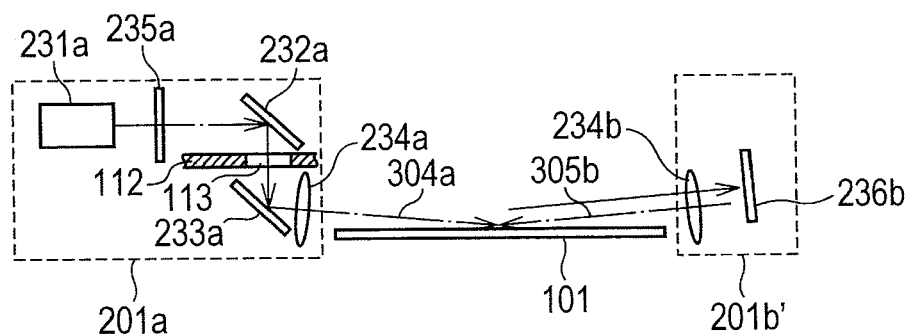
FIG. 3B is a front block diagram for showing an outline configuration of the illumination optical system subunit in the optical microscope of the review device in the embodiment of the present invention.
Figure 3C:
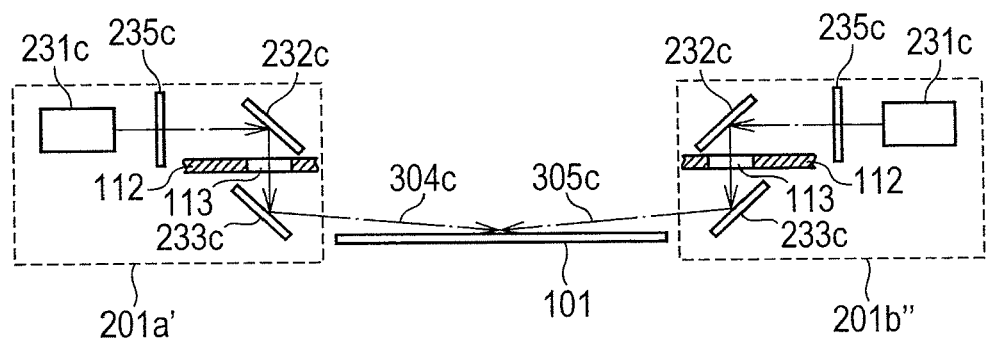
FIG. 3C is a front block diagram for showing an outline configuration of the illumination optical system subunit in the optical microscope of the review device in the embodiment of the present invention.

FIG. 3A, FIG. 3B, and FIG. 3C show configuration examples of the illumination optical system unit set 2011 using two illumination units 201 and modified examples 2012 and 2013 thereof.

FIG. 3A shows a configuration example of the illumination optical system unit set 2011 in which the light collecting irradiation-type illumination optical systems 201a and 201b having the same configuration are arranged to face each other. Each of the light collecting irradiation-type illumination optical systems 201a and 201b is configured by appropriately using a light source 231a, an epi-illumination mirror 232a that introduces a light beam emitted from the light source 231a to the vacuum chamber 112 to control the illumination position on the surface of the specimen 101, an irradiation mirror 233a that introduces the light beam introduced to inside the vacuum chamber 112 from the epi-illumination mirror 232a through a vacuum sealed window 113 to the specimen 101, a collecting lens 234a that collects and irradiates a light beam 304a or 305a introduced from the irradiation mirror 233a onto the specimen 101, and an optical isolator 235a that prevents a zero-order light reflected on the specimen 101 from entering the light source 231a. The illumination optical systems 201a and 201b irradiate the light beams 304a and 305a onto the specimen 101 under the angular conditions where the light beams 304a and 305a interfere with each other on the specimen 101.

The configuration example shown in FIG. 3A is advantageous in that the interference phenomena of the illumination lights 304a and 305a irradiated from the respective illumination optical systems 201a and 201b are hardly influenced by the state of the surface of the specimen 101.

FIG. 3B shows a configuration example of the reflection light collecting-type illumination optical system unit set 2012 using the illumination optical system 201a and an illumination optical system 201b'. The illumination optical system 201b' is configured by appropriately using a collecting lens 234b that parallelizes incident light that is obtained in such a manner that the light 304a collected and irradiated on the specimen 101 from the illumination optical system 201a is reflected on the specimen 101 and the reflected light enters the illumination optical system 201b', and a mirror 236b that vertically reflects the light parallelized by the collecting lens 234b. Further, the light 304a collected and irradiated from the illumination optical system 201a enter the collecting lens 234b while being expanded after reflected on the surface of the specimen 101 to become the parallel light, the parallel light is vertically reflected on the reflecting mirror 236b, and the vertically-reflected light is collected and irradiated onto the specimen 101 by a collecting lens 235b. The illumination optical systems 201a and 201b' irradiate the light beams 304a and 305b onto the specimen 101 under the angular conditions where the light beams 304a and 305b interfere with each other on the specimen 101.

In the configuration example shown in FIG. 3B, the number of constitutional elements of the illumination optical system unit set 2012 can be reduced.

FIG. 3C shows a configuration example in which an illumination optical system 201a' and an illumination optical system 201b'' that have the same configuration and that irradiate parallel light are arranged to face with each other. Each of the parallel irradiation-type illumination optical system 201a' and illumination optical systems 201b'' is configured by appropriately using a light source 231c, an epi-illumination mirror 232c that introduces a light beam irradiated from the light source 231c to the vacuum chamber 112 to control the illumination position on the surface of the specimen 101, an irradiation mirror 233c that introduces the light beam introduced from the epi-illumination mirror 232c through the vacuum sealed window 113 to the specimen 101, and an optical isolator 235c that prevents a zero-order light reflected on the specimen 101 from entering the light source 231c. The illumination optical systems 201a' and 201b'' irradiate the light beams 304c and 305c onto the specimen 101 under the angular conditions where the light beams 304c and 305c interfere with each other on the specimen 101.

The configuration shown in FIG. 3C can keep the width of the stationary waves constant in a wide range as compared to the light collecting irradiation-type illumination optical system unit set 2011 or 2012 shown in FIG. 3A and FIG. 3B. However, the configuration shown in FIG. 3C has no collecting lens 234a, and thus the illumination intensity becomes weaker as compared to that of the light collecting irradiation-type illumination optical system unit set 2011 or 2012 shown in FIG. 3A and FIG. 3B. Thus, when the scattered light from minute defects on the surface of the specimen 101 is detected, it is necessary to use a high-intensity light source for the light source 231c.

Figure 3D:
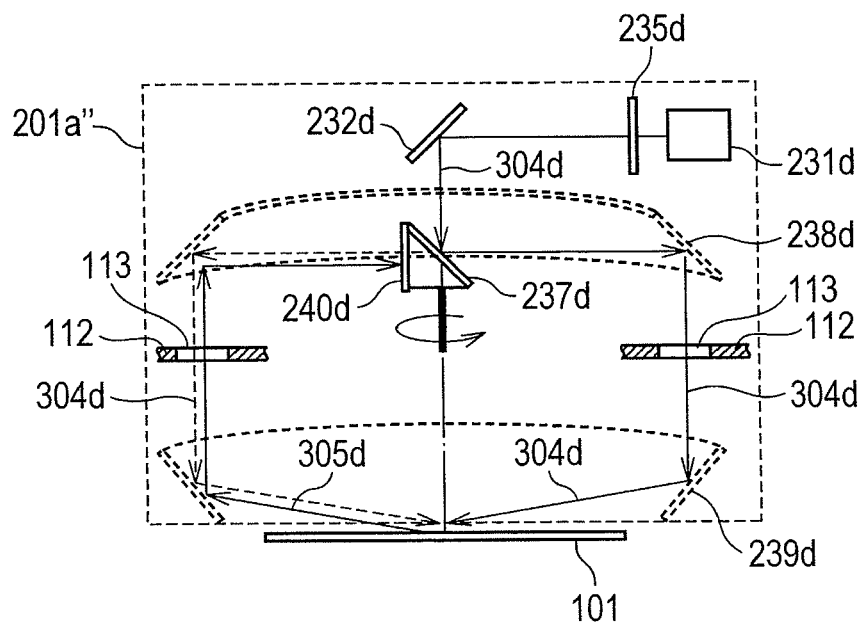
FIG. 3D is a front block diagram for showing an outline configuration of the illumination optical system subunit in the optical microscope of the review device in the embodiment of the present invention.

FIG. 3D shows a configuration example of an illumination optical system unit set 2014 that includes an illumination optical system 201a" having a function of changing the incidence plane orientation of illumination. Using the illumination optical system 201a" having a function of changing the incidence plane orientation of illumination, the illumination can be realized in an arbitrary incidence plane orientation using less constitutional elements. Further, the illumination can be realized in plural incidence plane orientations using less constitutional elements.

The illumination optical system unit set 2014 shown in FIG. 3D is configured by appropriately using a light source 231d, a rotating mirror 237d that reflects an illumination light 304d irradiated from the light source 231d to an arbitrary orientation, an epi-illumination conical mirror 238d that introduces the light beam 304d reflected on the rotating mirror 237d to the vacuum chamber 112 to control the illumination position on the surface of the specimen 101, an illumination conical mirror 239d that introduces the light beam 304d introduced from the epi-illumination conical mirror 238d through the vacuum sealed window 113 to the specimen 101, a rotating mirror 240d that vertically reflects a light that is collected and irradiated on the specimen 101 from the illumination conical mirror 239d and that is reflected on the specimen 101, the illumination conical mirror 239d, and the epi-illumination conical mirror 238d, and an optical isolator 235d that prevents a light 305d reflected on the rotating mirror 240d, the illumination conical mirror 239d, and the epi-illumination conical mirror 238d from entering the light source 231d.

Further, when the light is collected and irradiated on the specimen 101, a collecting lens 234d as described in FIG. 3A may be arranged on the optical path of each of the incident lights 304d and 305d. One axicon lens may be used for the collecting lens 234d to collect the incident lights 304d and 305d at the same time. Further, when collecting and irradiating the light, an irradiation mirror having an aspherical reflecting plane may be used as the irradiation mirror 239d. In this case, the reflected light collected and irradiated on the specimen 101 by the illumination conical mirror 239d become parallel light by the illumination conical mirror 239d to be reflected on the epi-illumination conical mirror 238d, and are vertically reflected on the rotating mirror 240d to be reflected on the rotating mirror 240d and the epi-illumination conical mirror 238d. Then, the light is collected and irradiated on the specimen 101 by the illumination conical mirror 239d. The epi-illumination conical mirror 238d and the illumination conical mirror 239d irradiate the light beams 304d and 305d onto the specimen 101 under the angular conditions where the light beams 304d and 305d interfere with each other on the specimen 101.

The rotating mirrors 237d and 240d have the same rotational axis center. Each of the epi-illumination conical mirror 238d and the illumination conical mirror 239d may be formed in a conical shape to reflect light in a range between orientation angles $-\pi$ and $\pi$ on the assumption that a certain angle relative to the axis center of the optical axis 301 of the detection optical system is 0, or may be formed in a shape in which a part of a conical shape is chipped. For example, each of the epi-illumination conical mirror 238d and the illumination conical mirror 239d may be formed in a halved shape to reflect light only in a range between orientation angles 0 and $\pi$ on the assumption that a certain angle is 0. In the case of the halved shape, beams in a range between $-\pi$ and 0 may be trapped to trap the light reflected on the specimen 101. The rotating mirrors 237d and 240d are rotated, so that the incidence planes of the illumination light 304d and 305d can have arbitrary orientations.

The rotational orientation angles of the rotating mirrors 237d and 240d are controlled by the control system 125 (FIG. 1). Further, the rotational orientation angles of the rotating mirrors 237d and 240d can be stored into the storage device 124 (FIG. 1) that stores detection signals obtained by the imaging element 207.

The illumination optical system unit sets 2011 to 2014 whose configuration examples are shown in FIG. 3A, FIG. 3B, FIG. 3C, and FIG. 3D, respectively, are moved in the height direction by the height control mechanism 209 that moves the objective lens 202 in the height direction. Further, in accordance with the amount of changes, in the height direction, of the height control mechanism 209 that moves the objective lens 202 to the height direction, another height control mechanism (not shown) different from the height control mechanism 209 that moves the illumination optical system unit 201 may be used. By shifting the illumination optical unit 201 in the height direction while being moved together with the objective lens 202, the stationary waves generated on the specimen 101 can be shifted relative to the surface of the specimen. Further, in the case where there is a possibility that the amount of changes in the height direction increases, the shift amount of the position of the plane 303 conjugate to the pupil plane 302 of the objective lens 202 increases, and thus the illumination optical system unit 201, the objective lens 202, and the space distribution optical element 205 may be moved in the height direction. Further, a zoom lens may be provided at the stage subsequent to the objective lens 202 to suppress the fluctuation of the position of the plane 303 conjugate to the pupil plane 302 of the objective lens 202.

The optical microscope 105 shown in FIG. 2 mounts any two sets of illumination optical system unit sets 2011 to 2013 whose configuration examples are shown in FIG. 3A, FIG. 3B, and FIG. 3C, respectively. In each of the configuration examples shown in FIG. 3A, FIG. 3B, and FIG. 3C, a laser light source is used as the light source 231a or 231c used in each of the illumination optical system unit sets 2011 to 2013. This configuration is advantageous when a large amount of illumination light is to be secured. On the other hand, from the viewpoint of improving the coherency of a laser, a single laser (not shown) is suitable for use as a light source in such a manner that the laser emitted from the single laser light source is divided into plural beams using a half mirror and a fiber to be transmitted to the light source 231a or 231c used in each of the illumination optical system unit sets 2011 to 2013.

Further, in the case of a configuration in which light reflected on the surface of the specimen 101 is allowed to return using the mirrors 236b and 240d that are vertically arranged relative to the optical axis of the light and to interfere near the surface of the specimen 101 as shown in the configuration example shown in each of FIGS. 3B and 3D, it is necessary to arrange the returning mirrors 236b and 240d at a coherence distance. Further, in the case where the incident light 304a and 305b or 304d and 305d are P polarization light in the configuration examples shown in FIGS. 3B and 3D, the incidence angle relative to the specimen 101 is preferably not near the Brewster angle. The reflectance ratio of the P polarization light is remarkably low near the Brewster angle. Thus, in the case of a configuration in which light reflected on the specimen 101 once is used as illumination light, the incidence angle should not be near the Brewster angle.

Next, the space distribution optical element 205 will be described using FIGS. 4A, 4B and 5.

Figure 4A:
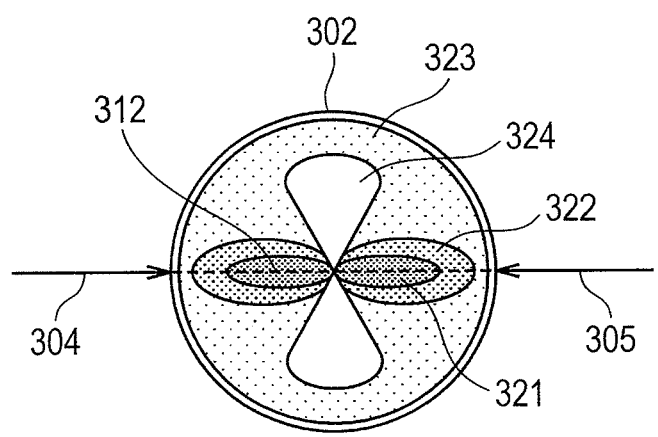
FIG. 4A shows an example of distribution of scattered light that can be obtained on or near a pupil plane in the optical microscope of the review device in the embodiment of the present invention, and is a diagram for showing distribution of scattered light from minute irregularities on a surface of a substrate.
Figure 4B:
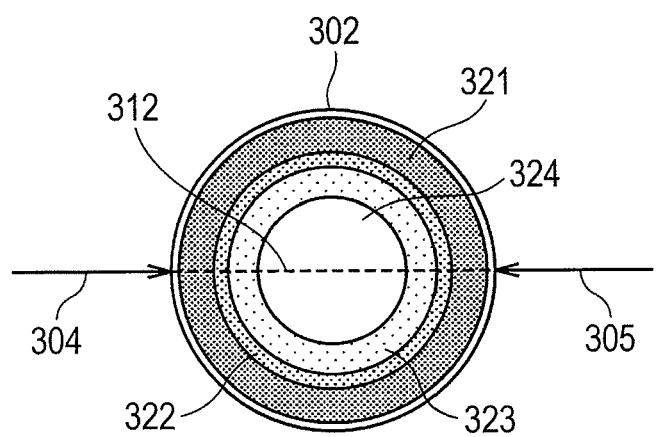
FIG. 4B shows an example of distribution of scattered light that can be obtained on or near the pupil plane in the optical microscope of the review device in the embodiment of the present invention, and is a diagram for showing distribution of scattered light from defects of foreign substances on the surface of the substrate.
Figure 5:
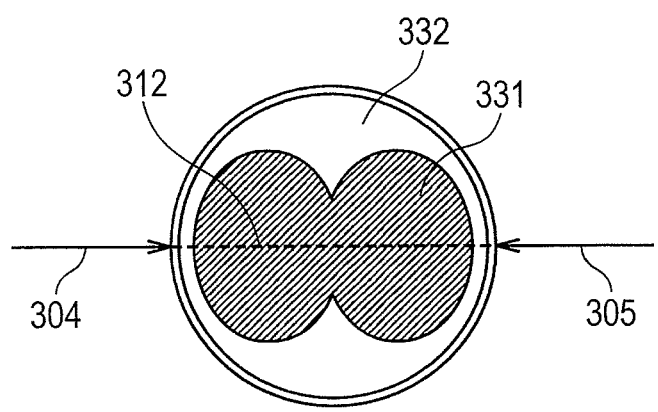
FIG. 5 is a plan view for showing a functional configuration of a spatial filter arranged on or near the pupil plane in the optical microscope of the review device in the embodiment of the present invention.

Each of FIGS. 4A and 4B shows an example of the intensity distribution of scattered light from a substrate having minute defects and roughness obtained using a scattered light simulation. Each of FIGS. 4A and 4B shows an example of the intensity distribution of radial polarization components of light scattered on the surface of the substrate after two illumination light 304 and 305 with a wavelength of 400 nm having the same incidence planes are allowed to enter, as P polarization illumination, the substrate having minute defects at the same incidence angle while being opposed to each other. It should be noted that the intensity distribution of scattered light to be obtained is not limited to radial polarization, but may be described using all intensities and polarization components. The polarization components may be radial polarization, azimuth polarization, linear polarization in which the polarization angle is inclined in a range between π and −π, or elliptical (circular) polarization.

Each of FIG. 4A and FIG. 4B shows the intensity distribution of scattered light in the pupil plane 302. An axis 312 in the intensity distribution shows an axis by which the incidence planes of the illumination lights 304 and 305 are associated with the pupil plane 302. The arrow 304 denotes an incidence direction of one illumination light (for example, the light beam 304a of FIG. 3A), and the arrow 305 denotes an incidence direction of the other illumination light (for example, the light beam 305a of FIG. 3A).

FIG. 4A shows the intensity distribution of radial polarization components of scattered light in which stationary wave illumination light generated by the illumination light 304 and 305 are scattered by roughness (minute irregularities that are not defects on the surface of the substrate) of the surface of the substrate 101, and FIG. 4B shows the intensity distribution of radial polarization components of scattered light scattered by minute defects. An area 321 in each of FIG. 4A and FIG. 4B denotes an area where the intensity of the scattered light is strong, an area 322 denotes an area where the intensity of the scattered light is slightly strong, an area 323 denotes an area where the intensity of the scattered light is slightly weak, and an area 324 denotes an area where the intensity of the scattered light is weak. The intensity distribution of the scattered light shows a relative relation between the intensities of the scattered light, and the same relative intensity display areas of the distributions of FIG. 4A and FIG. 4B do not necessarily indicate the same intensity (for example, the area 321 of FIG. 4A and the area 321 of FIG. 4B do not necessarily indicate the same intensity).

As the intensity distribution of scattered light shown in each of FIG. 4A and FIG. 4B, the distribution of scattered light from the illumination target is dependent on the shape of the illumination target. Further, although not shown in the drawing, the optical characteristics of the scattered light differ in the intensity distribution and the polarization distribution of the scattered light depending on the types, shapes, and directions of defects.

In the scattered light simulation described in each of FIG. 4A and FIG. 4B, the illumination light 304 and 305 are irradiated onto the specimen 101 from obliquely-upward directions, and the intensity distribution and the polarization distribution of the scattered light scattered by roughness on the surface of the specimen 101 or scattered by foreign substances or defect models arranged on the specimen 101 are calculated on the surface (pupil plane) nearest to the specimen 101 of the optical element nearest to the specimen 101 of the imaging optical system. The incidence illumination light may be only one light beam from one direction.

Further, by changing the vibration direction of light, namely, the polarization direction, the way the scattered light is generated is changed, and the scattered light from the specimen 101 can be suppressed or the scattered light from defects can be amplified. Therefore, the space distribution optical element 205 having a rotational photon function is appropriately set and arranged on the pupil plane 302 of the objective lens 202 of the optical microscope 105 shown in FIG. 2 or near the pupil plane 302, or on the plane 303 conjugate to the pupil plane of the objective lens 202 or near the plane 303 conjugate to the pupil plane of the objective lens, so that the ratio of the scattered light from the surface of the substrate to those from foreign substances can be increased, and high S/N defect detection can be realized. In the optical microscope 105 shown in FIG. 2, the space distribution optical element 205 is arranged on the plane 303 conjugate to the pupil plane 302 of the objective lens 202.

The space distribution optical element 205 is configured by appropriately using a phase shifter, a wavelength plate, a polarizer, a spatial filter, a neutral density filter, a liquid crystal optical element, a magnetooptical modulator, and photonic crystal, and has transmission characteristics with spatial distribution, optical rotation characteristics with spatial distribution, and transmission polarization direction selective characteristics with spatial distribution.

A method of determining the optical characteristics of the space distribution optical element 205, or the arrangement of the phase shifter configuring the space distribution optical element 205, the inclination of the delayed phase axis and the inclination of the advanced phase axis of the wavelength plate, the optical rotation direction by a polarization direction control device, the light blocking area in the spatial filter, the transmission polarization axis direction of the polarizer, the transmittance of the neutral density filter, voltage applied to the liquid crystal element, voltage applied to the magnetooptical modulator, and the optical characteristics of the photonic crystal is determined on the basis of the intensity distribution of scattered light obtained by the scattered light simulation described in each of FIG. 4A and FIG. 4B or by actual measurement.

Next, a method of determining the optical characteristics of the space distribution optical element 205 and the effects thereof will be described.

As a first example of the space distribution optical element 205, an example of a method of determining polarization transmission axis distribution h (r, θ), a configuration using a polarizer 231 for the space distribution optical element 205, and the effects thereof will be described.

First, scattered light intensity distribution fS (r, θ) from minute defects or minute foreign substances to be detected by the scattered light simulation at a high degree of sensitivity, radial polarization distribution $P_{SP}$ (r, θ) and S polarization distribution $P_{SS}$ (r, θ) of scattered light, scattered light intensity distribution fN (r, θ) from minute irregularities on the surface of the substrate, and P polarization distribution $P_{NP}$ (r, θ) and S polarization distribution $P_{NS}$ (r, θ) of scattered light are obtained.

Polarization transmission axis direction distribution h (r, θ) of the space distribution optical element 205 is determined as polarization axis distribution in which scattered light from the minute irregularities (roughness) on the surface of the substrate is blocked most, namely, h (r, θ) to minimize Π of (Equation 1), or polarization axis distribution in which scattered light from the minute defects or minute foreign substances is allowed to transmit most, namely, h (r, θ) to maximize Λ of (Equation 2), or polarization axis distribution in which the scattered light from the minute irregularities (roughness) on the surface of the substrate is blocked and the scattered light from the minute defects or minute foreign substances is allowed to transmit, namely, h (r, θ) to maximize Ω of (Equation 3).

[Equation 1]

$$\pi = \int \sqrt{|P_{NP}(r,\theta) \cdot h(r,\theta)|^2 + |P_{NS}(r,\theta) \cdot h(r,\theta)|^2} \, drd\theta \quad \text{(Equation 1)}$$

[Equation 2]

$$\Lambda = \int \sqrt{|P_{SP}(r,\theta) \cdot h(r,\theta)|^2 + |P_{SS}(r,\theta) \cdot h(r,\theta)|^2} \, drd\theta \quad \text{(Equation 2)}$$

[Equation 3]

$$\Omega = \frac{\int \sqrt{|P_{SP}(r,\theta) \cdot h(r,\theta)|^2 + |P_{SS}(r,\theta) \cdot h(r,\theta)|^2} \, drd\theta}{\int \sqrt{|P_{NP}(r,\theta) \cdot h(r,\theta)|^2 + |P_{NS}(r,\theta) \cdot h(r,\theta)|^2} \, drd\theta} \quad \text{(Equation 3)}$$

In this case, an area on the pupil plane 302 is divided into plural areas, and h (r, θ) to minimize Π of (Equation 1), h (r, θ) to maximize Λ of (Equation 2), and h (r, θ) to maximize Ω of (Equation 3) may be determined in each of the plural divided areas.

As described above, the scattered light from the specimen 1 can be suppressed by selecting the vibration direction of light, namely, the polarization direction. Therefore, the polarization direction in each area selected by the method as described above is set for the space distribution optical element 205 arranged on the pupil plane 302 of the objective lens 202, arranged on the position 303 conjugate to the pupil plane 302, or arranged near the position 303, so that the ratio of the scattered light from the surface of the substrate to those from the foreign substances can be increased, and high S/N defect detection can be realized.

Next, as a second example of a configuration of the space distribution optical element 205, a configuration in which a rotational photon function to control the polarization direction of the scattered light is provided for the space distribution optical element 205, the effects thereof, and a method of determining an optical rotation angle η (θ) will be described.

If the Fourier transform is performed for an image on the pupil plane 302, lights are overlapped with each other at the symmetrical points relative to the optical axis of the detection optical system on the pupil plane 302. In the case where the phases of vibration of the lights at the symmetrical points relative to the optical axis of the detection optical system on the pupil plane 302 are the same, the peak intensity is increased due to enhancement by overlapping. However, in the case where there are phase differences of Π, the intensity is cancelled and weakened.

For example, the radial polarization components of the scattered lights from the minute defects shown in FIG. 4B are isotropically distributed. Therefore, if the lights having the pupil plane intensity distribution as shown in FIG. 4B are collected and imaged, vibrational components in the direction (hereinafter, referred to as an XY direction) vertical to the optical axis of the detection system are cancelled, and only vibrational components in the direction (Z direction) parallel to the detection optical axis contribute to the peak intensity. In the case of an expansion system, NA on the image side is smaller than that on the object side, and the vibrational components in the Z direction are weaker than those in the XY direction. Thus, the peak intensity of an image of a minute object becomes weaker.

Therefore, as the optical rotation angle η(θ) of the rotational photons used for the space distribution optical element 205, any one of the optical rotation angle η(θ) at which the light vibrated in the h (r, θ) direction are cancelled by overlapping h (r, θ) to minimize Π of (Equation 1), the optical rotation angle η(θ) at which the light vibrated in the h (r, θ) direction are enhanced by overlapping h (r, θ) to maximize Λ of (Equation 2), and the optical rotation angle η(θ) at which the light vibrated in the h (r, θ) direction are enhanced by overlapping h (r, θ) to maximize Ω of (Equation 3) may be selected.

In this case, an area on the pupil plane 302 is divided into plural areas, each of the optical rotation angle η(θ) at which the lights vibrated in the h (r, θ) direction are cancelled by overlapping h (r, θ) to minimize Π of (Equation 1), the optical rotation angle η(θ) at which the lights vibrated in the h (r, θ) direction are enhanced by overlapping h (r, θ) to maximize Λ of (Equation 2), and the optical rotation angle η(θ) at which the lights vibrated in the h (r, θ) direction are enhanced by overlapping h (r, θ) to maximize Ω of (Equation 3) may be determined in each of the plural divided areas.

As described above, the scattered lights from the specimen 1 can be suppressed or the scattered lights from the defects can be amplified by changing the vibration direction of light, namely, the polarization direction. Therefore, the rotational photons are appropriately set and arranged on the pupil plane 302 or near the pupil plane 302, so that the ratio of the scattered lights from the surface of the substrate to those from the foreign substances can be increased, and high S/N defect detection can be realized.

Further, as a third example of a configuration of the space distribution optical element 205, the effects using a spatial filter as the space distribution optical element 205 and an example of a method of determining a light blocking area g (r, θ) of the spatial filter will be described.

As the spatial filter used for the space distribution optical element 205, the ratio of the amount of scattered light from the foreign substances to that on the surface of the substrate is derived by the scattered light simulation or actual measurement, light in an area where the ratio is larger than a threshold value is allowed to transmit, and light in an area where the ratio of the scattered light from the defects or foreign substances to those from the surface of the specimen is smaller than a threshold value is blocked. Then, the scattered light components are removed from the area where the ratio of the scattered light from the defects or foreign substances to those from the surface of the specimen is smaller than the threshold value, so that the ratio of the amount of scattered light from the defects or foreign substances to that from the specimen can be increased on the entire pupil plane.

As a method of determining the light blocking area g (r, θ) of the spatial filter, there is a method of optimizing the light blocking area g (r, θ) as maximizing Ψ shown in, for example, (Equation 4).

[Equation 4]

$$\psi = \frac{\int f_S(r, \theta) \times g(r, \theta) dr d\theta}{\int f_N(r, \theta) \times g(r, \theta) dr d\theta}$$

(Equation 4)

Further, an area on the pupil plane 302 is divided into plural areas, and the area where the ratio of the scattered light from the specimen to those from the foreign substances is smaller than the threshold value may be determined as the light blocking area g (r, θ) in each of the plural divided areas.

As described above, the spatial filter is appropriately set and arranged, so that the ratio of the scattered light from the specimen to those from the foreign substances can be increased, and high S/N defect detection can be realized. Further, the spatial filter used to remove diffraction light from a pattern may be used for the configuration of the space distribution optical element 205.

Next, an example of the effects of the space distribution optical element 205 will be described with reference to FIG. 5 using the example of the radial polarization components of the scattered light scattered from the minute defects described using FIG. 4A and FIG. 4B.

The space distribution optical element 205 having a spatial filter function that blocks areas 312 and 331 where the amount of light of radial polarization components of scattered light from the substrate having the roughness is larger than that from the minute defects and a rotational photon function that has spatially-different optical rotation angle distributions in which radial polarization passing through an area 332 other than the area 312 is uniformly converted into parallel polarization directions is arranged on the pupil plane of the objective lens 202 or near the pupil plane, so that the ratio of the amount of scattered light from the substrate to that from the defects can be increased. Further, the peak intensity of the scattered light from the defects can be intensified at the time of forming an image, and high S/N defect detection can be realized. Further, in the case of using illumination light having the same incidence planes and arranged to face each other, the space distribution optical element 205 is provided with optical characteristics symmetric relative to the incidence plane of the illumination light.

Further, in the case where the incidence planes of the illumination lights having the same incidence planes and arranged to face each other are changed, or in the case where the illumination lights are changed, the space distribution optical element 205 is rotated in accordance with the incidence planes of the illumination lights. Alternatively, in the case where the incidence planes of the illumination lights are changed, one of the plural space distribution optical elements 205 is selected in accordance with the incidence planes of the illumination lights, so that the space distribution optical element 205 may be switched to another.

Figure 6:
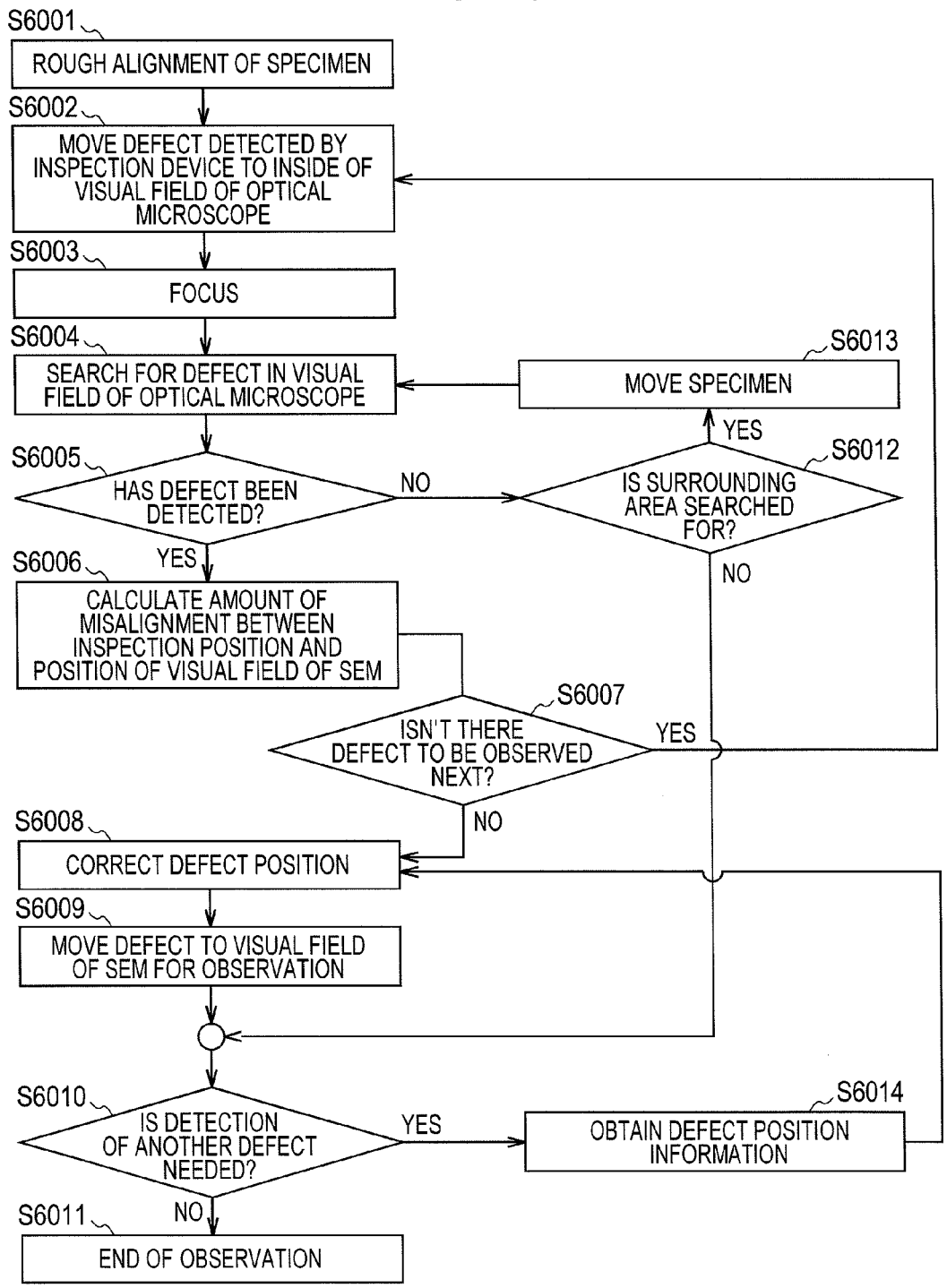
FIG. 6 is a flowchart for explaining a procedure of observing defects using the review device in the embodiment of the present invention.

Next, a flow of processes in which the defects detected by the inspection device 107 (FIG. 1) are observed by the review device 100 described in FIG. 1 will be described using FIG. 6.

First, the defects on the specimen 101 are detected using the inspection device 107, and the inspection device 107 outputs inspection information of the specimen 101 via the network 121 to be input into the storage device 124 of the review device 100. The inspection information of the specimen 101 output from the inspection device 107 is inspection information configured by using an inspection result configured by using any one of or a combination of a defect coordinate, a defect signal, a defect shape, polarization of scattered light of defects, a defect type, a defect label, the characteristic amount of defects, and a scattered signal on the surface of the specimen 101, and an inspection condition configured by using any one of or a combination of the illumination incidence angle of the inspection device 107, an illumination wavelength, the azimuth angle of illumination, illumination intensity, illumination polarization, the azimuth angle of the detection unit, the elevation angle of the detection unit, and the detection area of the detection unit. In the case where there are plural detectors in the inspection device, inspection information obtained as a result of inspecting the specimen 101 output from each detector, or inspection information of the specimen 101 obtained by integrating outputs from the plural detectors is used.

Next, a part or all of defects extracted from those detected by the inspection device 107 is observed by the review device 100 using the information stored in the storage device 124.

First, rough alignment of the specimen 101 is carried out (S6001). The rough alignment is carried out by a bright-field observation using the optical microscope 105. Next, the stage 103 of the review device 100 is moved so that the defects to be observed on the specimen 101 falls within the visual field of the optical microscope 105 using the positional information of the defects preliminarily detected by another inspection device 107 on the basis of the defect coordinate obtained by the inspection device 107 (S6002). Next, the objective lens 202 is moved by the height control mechanism 209 to be focused (S6003).

Next, the defects are searched for using the image obtained by the optical microscope 105 and the imaging element 207 (S6004). If the defects are detected (S6005—YES), the amount of misalignment of the position of the visual field of the SEM 106 relative to the defects when the defects are to be observed by the SEM 106 using the positional information of the defects preliminarily detected by another defect inspection device on the basis of a difference between the defect detection position by the optical microscope 105 and the positional information of the defects preliminarily detected by another defect inspection device is calculated (S6006).

While calculating the amount of misalignment of the position of the detected defects, it is checked whether or not there is another defect to be observed next (S6007). In the case where the result shows that there is another defect to be observed (in the case of YES in the determination of S6007), the flow returns to S6002 in which the stage 103 is controlled so that the defect to be observed next is moved to the inside of the visual field of the optical microscope on the basis of the positional information of the defect to be observed next stored in the storage device 124. Then, steps of S6003 to S6006 are executed.

In the case where it is determined that there is no defect to be observed in S6007 (in the case of NO in the determination of S6007), the positional information detected by the coordinate system of another defect inspection device is corrected to the positional information in the coordinate system of the review device 100 for defects that were preliminarily detected by another defect inspection device but were not detected by the optical microscope 105 on the basis of the amount of misalignment between the positional information of the observed defects calculated in S6006 and preliminarily detected by another defect inspection device and visual field positional information (positional information in the coordinate system of the review device 100) of the SEM 106 (S6008). Next, the stage 103 on which the specimen 101 is mounted is moved from the position of the optical microscope 105 to the position of the SEM 112, and the defects with the positional information corrected are moved to the visual field of the SEM 106 to observe the defects (S6009). In this case, the observed information is transmitted to the control system 125 and is registered in the database 122.

Next, in the case where there is no need of other defect information (S6010—NO), the observation is terminated (S6011). In the case where the observation is needed (S6010—YES), the positional information of the defects to be observed is obtained, and the flow returns to S6008 to proceed with the process. It should be noted that in the case where no defects are detected by the above-described defect detection procedure (S6005—NO), it is conceivable that the defects are located out of the visual field of the optical microscope 105. Thus, surrounding areas of the visual field of the optical microscope 105 may be searched for. In the case where the surrounding areas are searched for (S6012—YES), the specimen 101 is moved by a distance corresponding to the visual field (S6013) to perform the process from the above-described defect detection procedure. Further, in the case where the surrounding areas are not searched for (S6012—NO), the process is performed in accordance with the procedure.

Figure 7:
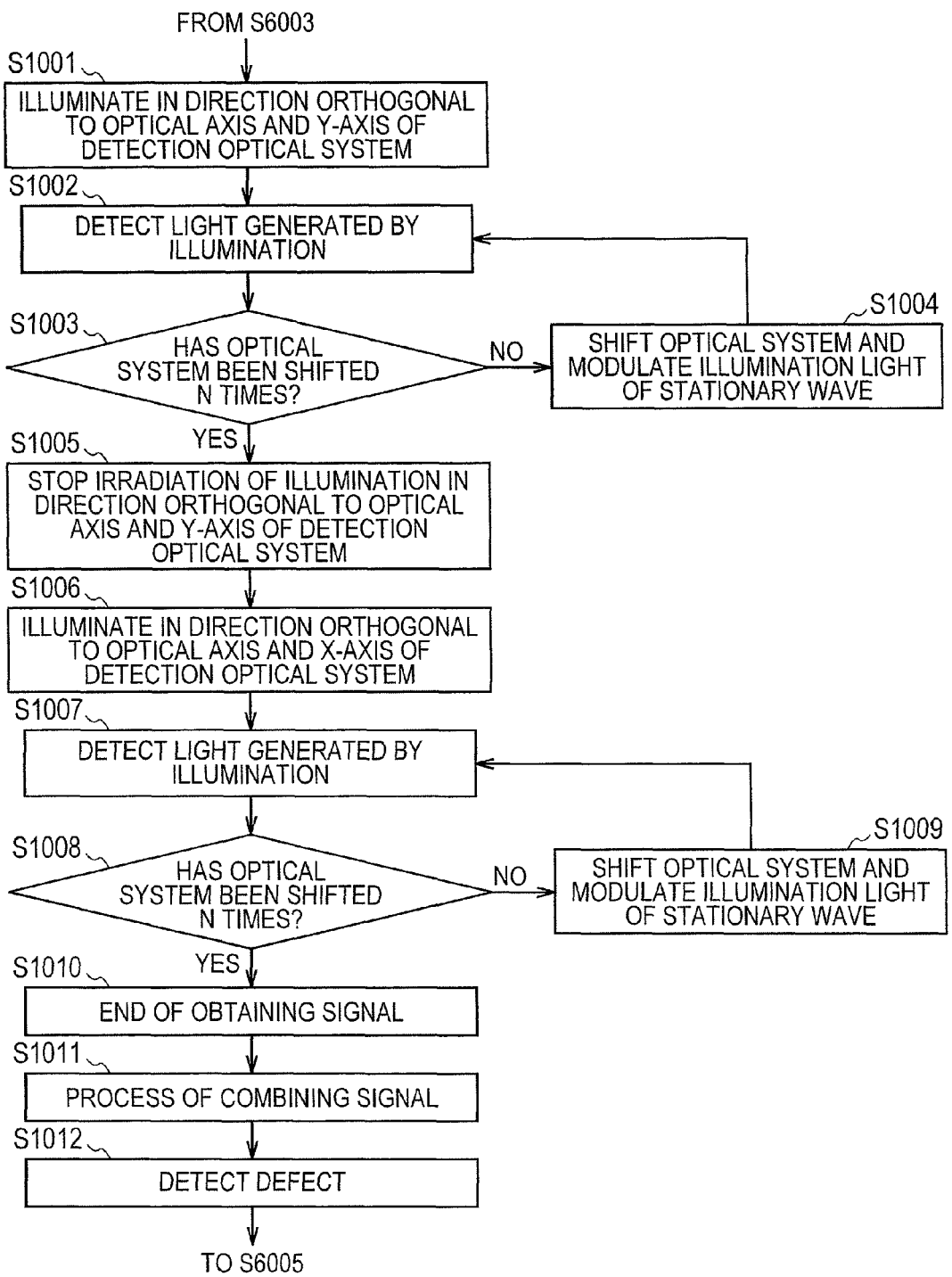
FIG. 7 is a flowchart for explaining a procedure of detecting defects using the optical microscope of the review device in the embodiment of the present invention.

Next, a flow of processes of obtaining a high-resolution image in S6004 in which defects are searched for within the visual field of the optical microscope in the processing flow in which the observation is performed by the review device 100 described in FIG. 6 using the optical microscope 105 in the configuration example having two sets of illumination optical system unit sets 2011 of FIG. 3A will be described using FIG. 7.

First, illumination lights having the same incidence planes are irradiated on the specimen 101 from directions opposite to each other by a first illumination optical system unit set 2011 so that the illumination lights interfere with each other (S1001), and light scattered on the specimen 101 by stationary waves generated on the specimen 101 due to the interference is detected using the detector 207 (S1002).

Next, the positions of the objective lens 202 and the illumination optical system unit 201 are changed in the height direction by the height control mechanism 209 (S1003—NO: the amount of deviation in the height direction corresponds to an amount of $\pi/N$ of the phase change of the stationary waves on the surface of the specimen 101 generated by changing in the height direction), and the phase of the stationary waves generated on the specimen 101 is modulated by the illumination lights 304a and 305a (S1004). The scattered light on the specimen 101 generated from the modulated stationary waves is detected by the detector 207 (S1002). The steps S1002, S1003, and S1004 are repeated N times until the preliminarily-set number of times of shift can be obtained. In the case where the steps S1002, S1003, and S1004 are repeated N times and (N+1) signals are obtained (S1003—YES), the illumination lights from the first illumination optical system unit 2011 are blocked so as not to enter the specimen 101 (S1005), the illumination lights having the same incidence planes are irradiated on the specimen 101 from directions opposite to each other by a second illumination optical system unit 2011 (S1006), and light scattered on the specimen 101 by stationary waves generated on the specimen 101 is detected using the detector 207 (S1007).

Next, the positions of the objective lens 202 and the illumination optical system unit 201 are changed in the height direction by the height control mechanism 209 (S1008—NO), and the phase of the stationary waves generated on the specimen 101 is modulated by the illumination lights 304 and 305 (S1009). The scattered light on the specimen 101 generated from the modulated stationary waves is detected by the detector 207 (S1007). The steps S1007, S1008, and S1009 are repeated N times until the preliminarily-set number of times of shift can be obtained. In the case where the steps S1007, S1008, and S1009 are repeated N times and (N+1) signals are obtained (S1008—YES), the process of obtaining the signals is completed (S1010).

Next, the 2 (N+1) signals obtained as described above are combined in a frequency space, the combined signal is inversely converted, and signals with a higher degree of resolution than the signals obtained by the detector 207 are combined (S1011). Finally, the signal (image) with a higher degree of resolution combined in S1011 is processed to detect defects, and the coordinates of the detected defects are obtained (S1012). In S6006 of the flowchart shown in FIG. 6, the coordinate information of the defects obtained in S1012 is compared to the positional information of the defects preliminarily detected by another defect inspection device, and the amount of misalignment between the positional coordinates of the defects detected by another defect inspection device and the positional coordinates of the defects observed by the SEM 106 is calculated.

In the case where the amounts of deviation of the objective lens 202 and the illumination optical system unit 201 in the height direction by the height control mechanism 209 are large in S1003 and S1008, not only the position of the objective lens 201, but also the position of the detect optical system 201 may be changed in the height direction.

Further, in the case of the configuration of the illumination optical system unit 201a" shown in FIG. 3D, instead of S1005 and S1006, the rotating mirrors 237d and 240d are rotated, illumination lights having incidence planes different from those of illumination lights before rotation are irradiated to face each other, and the illumination of stationary waves may be generated. Further, the angles of the rotating mirrors 237d and 240d may be set on the basis of the information obtained by the inspection device 107 or the information obtained at the time of the bright-field observation of the optical microscope 105.

As another method, an optical filter with an appropriate density may be set to adjust the illumination intensity of the optical microscope 105 on the basis of the brightness information obtained by the inspection device 107, or in the case of intensity-variable illumination, the illumination intensity in accordance with the size of the defects may be promptly set by adjusting the intensity of illumination itself. In this case, ghost that is likely to happen to an enormous defect and deterioration of the accuracy of coordinates can be suppressed, and the inspection time can be shortened. In addition, the detection ratio of defects and the accuracy of coordinates can be improved.

Further, in the case where the detection device has plural sensors and scattered light with different scattering angles can be captured, the orientation and shape of the target defect can be estimated on the basis of the difference of an output of each sensor. On the basis of the estimation, highly-sensitive defect detection can be realized by setting optical conditions such as the rotational angles of the rotating mirrors 237*d* and 240*d*.

Next, the effects obtained by processing plural signals obtained after stationary waves are irradiated on the specimen 101, the illumination of the stationary waves is modulated, and lights generated on the specimen 101 in each modulation condition are detected by the detector 207 will be briefly explained.

In general, imaging distribution is expressed by convolution of a point image distribution function and scattered light distribution. If the illumination intensity is modulated, the point image distribution function is not changed, but the scattered light distribution is modulated. Thus, the imaging distribution is changed. The scattered light distribution is a product of the illumination light distribution and an object shape, and the illumination light distribution is already known.

This will be explained using a frequency space. For example, the Fourier-transformed imaging distribution function is expressed by a product of the Fourier-transformed point image distribution function and the Fourier-transformed scattered light distribution. Obtaining plural signals that are different in the illumination distribution function is equivalent to increasing the number of equations expressing the imaging distribution, the point image distribution function, and the scattered light distribution. Therefore, the illumination distribution is modulated, lights generated on the specimen 101 in each modulation condition are obtained by the detector 207, and the obtained plural signals are integrated. Thus, the shape of an object can be derived with a higher degree of accuracy than the signal obtained in one condition.

In the case where the stationary waves of the illumination lights irradiated from two directions are used as illumination, the resolution of illumination in the incidence direction is improved in the configuration, but the resolution in the direction orthogonal to the incidence plane of the illumination is not improved. Thus, the stationary waves generated on the specimen 101 are shifted, and the lights scattered on the specimen 101 are obtained in each of plural illumination conditions in the embodiment. The stationary waves generated on the specimen 101 can be shifted by shifting the positions of the objective lens 202 and the illumination optical system unit 201 in the height direction.

The invention achieved by the inventors has been concretely described above on the basis of the embodiment. However, it is obvious that the present invention is not limited to the above-described embodiment, but can be variously changed without departing from the gist of the present invention.

DESCRIPTION OF SYMBOLS

101 . . . specimen 102 . . . specimen holder 103 . . . stage 104 . . . optical height detection system 105 . . . optical microscope 106 . . . SEM 107 . . . inspection device 111 . . . vacuum sealed window 112 . . . user interface 124 . . . storage device 125 . . . control system 209 . . . height control mechanism

What is claimed is:

1. A defect observation method, comprising the steps of:
   detecting defects on a specimen detected by an inspection device using a detection device having an optical microscope on the basis of positional information of the defects;
   amending positional information of the defects on the specimen detected by the inspection device on the basis of positional information of the defects detected by the detection device having the optical microscope; and
   observing the defects detected by the inspection device by using an SEM (Scanning Electron Microscope) on the basis of the amended positional information,
   wherein the defects on the specimen detected by the inspection device are detected by the detection device having the optical microscope by:
   forming stationary waves on the specimen by allowing two illumination lights having a same wavelength to enter a same incidence plane of the specimen at a same incidence angle from directions that are opposite to each other and interfering with each other;
   removing scattered light components generated from minute irregularities on a surface of the specimen among scattered light from the specimen on which the stationary waves are formed by a spatial filter;
   detecting an image of scattered light from the specimen that are not removed by the spatial filter; and
   processing the detected image of the scattered light to detect the defects on the specimen detected by the inspection device.

2. The defect observation method according to claim 1, wherein the scattered light components generated from the minute irregularities on the surface of the specimen are removed using the spatial filter having any one of a function of controlling the polarization direction of the scattered light generated from the surface of the specimen, a function of selecting the polarization direction to transmit, and a function of selecting the transmittance of light.

3. A defect observation method, comprising the steps of:
   detecting defects on a specimen detected by an inspection device using a detection device having an optical microscope on the basis of positional information of the defects;
   amending positional information of the defects on the specimen detected by the inspection device on the basis of positional information of the defects detected by the detection device having the optical microscope; and
   observing the defects detected by the inspection device by using an SEM (Scanning Electron Microscope) on the basis of the amended positional information,
   wherein the defects on the specimen detected by the inspection device are detected by the detection device having the optical microscope by:
   forming stationary waves on the specimen by allowing two illumination lights having a same wavelength to enter a same incidence plane of the specimen at a same incidence angle from directions that are opposite to each other and interfering with each other;
   removing scattered light components generated from minute irregularities on a surface of the specimen among scattered light from the specimen on which the stationary waves are formed by a spatial filter;
   detecting an image of scattered light from the specimen that are not removed by the spatial filter; and
   processing the detected image of the scattered light to detect the defects on the specimen detected by the inspection device, wherein the image of the scattered light from the specimen that are not removed by the spatial filter is detected in such a manner that plural images of the scattered light from the specimen that are not removed by the spatial filter among those generated from the specimen are detected while changing the phase of the stationary waves formed on the specimen, and the plural detected images of the scattered light are processed to detect the defects on the specimen detected by the inspection device in such a manner that the plural detected images of the scattered light are combined to produce a combined image and the defects on the specimen detected by the inspection device are extracted by processing the produced combined image.

4. The defect observation method according to claim 3, wherein the process in which the two illumination lights having the same wavelength are allowed to enter the same incidence plane of the specimen at the same incidence angle from directions that are opposite to each other and are allowed to interfere with each other so that the stationary waves are formed on the specimen is performed on two incidence planes that cross each other.

5. A defect observation device comprising:
a detector that has an optical microscope;
a processor that amends positional information of defects on a specimen detected by an inspection device on the basis of a result of detecting the defects on the specimen detected by the inspection device using the detector on the basis of the positional information of the defects;
a defect observation device that observes the defects on the specimen detected by the inspection device using an SEM (Scanning Electron Microscope) on the basis of the positional information of the defects on the specimen amended by the processing unit;
a table on which the specimen is mounted and which is movable between the detector and the defect observation device; and
a controller configured to control the detector, the processor, the defect observation device, and the table,
wherein the detector includes:
  an illuminator that functions in such a manner that two illumination lights having a same wavelength are allowed to enter a same incidence plane of the specimen mounted on the table at a same incidence angle from directions that are opposite to each other and are allowed to interfere with each other so that stationary waves are formed on the specimen to illuminate a surface of the specimen;
  a detection optical system that has a spatial filter that removes scattered light components generated from minute irregularities on the surface of the specimen among scattered light from the surface of the specimen on which the stationary waves formed by the illuminator are illuminated and that forms an image of scattered light from the surface of the specimen that are not removed by the spatial filter; and
  an image detector that detects the image of the scattered light from the surface of the specimen formed by the detection optical system, and
wherein the controller is configured to detect the defects on the specimen detected by the inspection device by processing the image of the scattered light from the surface of the specimen detected by the image detector and amends the positional information of the defects on the specimen detected by the inspection device on the basis of the positional information of the detected defects on the table.

6. The defect observation device according to claim 5, wherein the spatial filter of the detection optical system has any one of a function of controlling a polarization direction of the scattered light generated from the surface of the specimen, a function of selecting the polarization direction to transmit, and a function of selecting a transmittance of light, and removes the scattered light components generated from the minute irregularities on the surface of the specimen.

7. A defect observation device comprising:
a detector that has an optical microscope;
a processor that amends positional information of defects on a specimen detected by an inspection device on the basis of a result of detecting the defects on the specimen detected by the inspection device using the detector on the basis of the positional information of the defects;
a defect observation device that observes the defects on the specimen detected by the inspection device using an SEM (Scanning Electron Microscope) on the basis of the positional information of the defects on the specimen amended by the processing unit;
a table on which the specimen is mounted and which is movable between the detector and the defect observation device; and
a controller configured to control the detector, the processor, the defect observation device, and the table,
wherein the detector includes:
  an illuminator that functions in such a manner that two illumination lights having a same wavelength are allowed to enter a same incidence plane of the specimen mounted on the table at a same incidence angle from directions that are opposite to each other and are allowed to interfere with each other so that stationary waves are formed on the specimen to illuminate a surface of the specimen;
  a detection optical system that has a spatial filter that removes scattered light components generated from minute irregularities on the surface of the specimen among scattered light from the surface of the specimen on which the stationary waves formed by the illuminator are illuminated and that forms an image of scattered light from the surface of the specimen that are not removed by the spatial filter; and
  an image detector that detects the image of the scattered light from the surface of the specimen formed by the detection optical system,
wherein the controller is configured to detect the defects on the specimen detected by the inspection device by processing the image of the scattered light from the surface of the specimen detected by the image detector and amends the positional information of the defects on the specimen detected by the inspection device on the basis of the positional information of the detected defects on the table, and
wherein the illuminator illuminates the specimen while sequentially changing states of the stationary waves formed on the specimen by changing the incident height of the two illumination lights onto the specimen, the image detector sequentially detects the image of the scattered light from the specimen that are not removed by the spatial filter among those from the surface of the specimen on which the stationary waves whose states are sequentially changed are illuminated, and the processor forms a combined image using the sequentially-detected images to detect the defects on the specimen detected by the inspection device by processing the formed combined image.

8. The defect observation device according to claim 7, wherein the illuminator includes a first illumination system that functions in such a manner that first two illumination lights having the same wavelength are allowed to enter a first incidence plane of the specimen at the same incidence angle from directions that are opposite to each other and are allowed to interfere with each other, and a second illumination system that functions in such a manner that second two illumination lights having the same wavelength are allowed to enter a second incidence plane orthogonal to the first incidence plane of the specimen at the same incidence angle from directions that are opposite to each other and are allowed to interfere with each other.

9. The defect observation method according to claim 3, wherein the image of the scattered light from the specimen that are not removed by the spatial filter is detected in such a manner that plural images of the scattered light from the specimen that are not removed by the spatial filter among those generated from the specimen are detected while changing the phase of the stationary waves formed on the specimen, and the plural detected images of the scattered light are processed to detect the defects on the specimen detected by the inspection device in such a manner that the plural detected images of the scattered light are combined to produce a combined image and the defects on the specimen detected by the inspection device are extracted by processing the produced combined image.

10. The defect observation method according to claim 3, wherein the process in which the two illumination lights having the same wavelength are allowed to enter the same incidence plane of the specimen at the same incidence angle from directions that are opposite to each other and are allowed to interfere with each other so that the stationary waves are formed on the specimen is performed on two incidence planes that cross each other.

11. The defect observation device according to claim 7, wherein the illuminator illuminates the specimen while sequentially changing the states of the stationary waves formed on the specimen by changing the incident height of the two illumination light onto the specimen, the image detector sequentially detects the image of the scattered light from the specimen that are not removed by the spatial filter among those from the surface of the specimen on which the stationary waves whose states are sequentially changed are illuminated, and the processor forms a combined image using the sequentially-detected images to detect the defects on the specimen detected by the inspection device by processing the formed combined image.

12. The defect observation device according to claim 7, wherein the illuminator includes a first illumination system that functions in such a manner that first two illumination lights having the same wavelength are allowed to enter a first incidence plane of the specimen at the same incidence angle from directions that are opposite to each other and are allowed to interfere with each other, and a second illumination system that functions in such a manner that second two illumination lights having the same wavelength are allowed to enter a second incidence plane orthogonal to the first incidence plane of the specimen at the same incidence angle from directions that are opposite to each other and are allowed to interfere with each other.

13. The defect observation method according to claim 1, wherein the image of the scattered light from the specimen that are not removed by the spatial filter is detected in such a manner that plural images of the scattered light from the specimen that are not removed by the spatial filter among those generated from the specimen are detected while changing the phase of the stationary waves formed on the specimen, and the plural detected images of the scattered light are processed to detect the defects on the specimen detected by the inspection device in such a manner that the plural detected images of the scattered light are combined to produce a combined image and the defects on the specimen detected by the inspection device are extracted by processing the produced combined image.

14. The defect observation method according to claim 3, wherein the scattered light components generated from the minute irregularities on the surface of the specimen are removed using the spatial filter having any one of a function of controlling the polarization direction of the scattered light generated from the surface of the specimen, a function of selecting the polarization direction to transmit, and a function of selecting the transmittance of light.

15. The defect observation device according to claim 5, wherein the illuminator includes a first illumination system that functions in such a manner that first two illumination lights having the same wavelength are allowed to enter a first incidence plane of the specimen at the same incidence angle from directions that are opposite to each other and are allowed to interfere with each other, and a second illumination system that functions in such a manner that second two illumination lights having the same wavelength are allowed to enter a second incidence plane orthogonal to the first incidence plane of the specimen at the same incidence angle from directions that are opposite to each other and are allowed to interfere with each other.

16. The defect observation device according to claim 7, wherein the spatial filter of the detection optical system has any one of a function of controlling a polarization direction of the scattered light generated from the surface of the specimen, a function of selecting the polarization direction to transmit, and a function of selecting a transmittance of light, and removes the scattered light components generated from the minute irregularities on the surface of the specimen.

17. The defect observation method according to claim 1, wherein said step of detecting an image of scattered light from the specimen that are not removed by the spatial filter is performed while changing a phase of the stationary waves.

18. The defect observation device according to claim 5, wherein the detection optical system is further configured to change a phase of the stationary waves during said step of detecting an image of scattered light from the specimen that are not removed by the spatial filter.

* * * * *